(12) United States Patent
Dyke et al.

(10) Patent No.: US 8,754,248 B2
(45) Date of Patent: Jun. 17, 2014

(54) PROCESS FOR PREPARING CATIONIC RUTHENIUM COMPLEXES

(75) Inventors: Alan Malcolm Dyke, Cambridge (GB); Hans Guenter Nedden, Cambridge (GB)

(73) Assignee: Johnson Matthey Public Limited Company, London (GB)

( * ) Notice: Subject to any disclaimer, the term of this patent is extended or adjusted under 35 U.S.C. 154(b) by 327 days.

(21) Appl. No.: 13/132,723

(22) PCT Filed: Dec. 3, 2009

(86) PCT No.: PCT/GB2009/051642
§ 371 (c)(1),
(2), (4) Date: Aug. 22, 2011

(87) PCT Pub. No.: WO2010/064045
PCT Pub. Date: Jun. 10, 2010

(65) Prior Publication Data
US 2011/0295008 A1 Dec. 1, 2011

(30) Foreign Application Priority Data
Dec. 3, 2008 (GB) .................................. 0822064.2

(51) Int. Cl.
*C07F 15/00* (2006.01)
*B01J 31/18* (2006.01)

(52) U.S. Cl.
USPC .......................................... 556/21; 502/155

(58) Field of Classification Search
USPC ..................................... 556/21, 136; 502/155
See application file for complete search history.

(56) References Cited

FOREIGN PATENT DOCUMENTS

| CN | 1727328 | 2/2006 |
|---|---|---|
| EP | 0366390 | 5/1990 |
| GB | 928441 | 6/1963 |
| GB | 2332201 | 6/1999 |
| WO | 2005007662 | 1/2005 |
| WO | 2007005550 | 1/2007 |
| WO | 2007123957 | 11/2007 |

OTHER PUBLICATIONS

Mashima, K. et al.: Cationic BINAP-Ru(II)halide complexes: Highly efficient catalysts for stereoselective asymmetric hydrogenation of alpha and beta-functionalized ketones. J. Org. Chem., vol. 59, pp. 3064-3076, 1994.*
International Search Report dated May 12, 2010, application No. PCT/GB2009/051642.
Wu et al.: "A New Chiral Dipyridylphosphine Ligand Xyl-P-Phos and Its Application in the Ru-catalyzed Asymmetric Hydrogenation of Beta-Ketoesters", Tetrahedron Letters, vol. 43, No. 8, Feb. 18, 2002, pp. 1539-1543.
Wu et al.: "Studies on the Rhodium- and Ruthenium—Catalyzed Asymmetric Hydrogenation of Alpha-Dehydroamino Acids Using a Family of Chiral Dipyridylphosphine Ligand (P-Phos)" Tetrahedron Asymmetry, vol. 14, No. 8, Apr. 18, 2003, pp. 987-992.
Wu et al.: "Air-Stable Catalysts for Highly Efficient and Enantioselective Hydrogenation of Aromatic Ketones", Journal of Organic Chemistry, vol. 67, No. 22, Nov. 1, 2002, pp. 7908-7910.
Grasa et al.: "A Chiral [(Dipyridylphosphine) RuCl2(1,3-Diphenylpropanediamine)] Catalyst for the Hydrogenation of Aromatic Ketones", Journal of Organometallic Chemistry, vol. 691, No. 10, May 1, 2006, pp. 2332-2334.
Great Britain Search Report dated Jul. 1, 2009, application No. GB0822064.2.
Evans et al.: Synthesis and Reactivity in Inorganic and Metal-Organic Chemistry, 2001, vol. 31(4), pp. 623-632.
Tsuno et al.: Synthesis of Chiral-at-Metal Half-Sandwich Ruthenium(II) Complexes with the CpH(PNMent) Tripod Ligand, Journal of Organometallic Chemistry, 2006, vol. 691, (12), pp. 2739-2747.
Great Britain Search Report dated Mar. 26, 2009, application No. GB0822064.2.
Wu et al., Synlett, 2001, vol. SI (Spec. Issue), pp. 1050-1054, Apr. 1, 2001.
Faraone et al., Inorganica Chimica Acta, 1979, vol. 34, pp. L251-L253.
Tang et al.: "New Chiral Phosphorus Ligands for Enantioselective Hydrogenation", Department of Chemistry, Chemical Reviews, 2003, vol. 103, No. 8, pp. 3029-3069.
Carretero et al., "Recent Applications of Chiral Ferrocene Ligands In Asymmetric Catalysis", Angew. Chem. Int. Ed., 2006, 45, pp. 7674-7715.
Shimizu et al.: "Recent Advances in Biaryl-Type Bisphosphine Ligands", Tetrahedron 61 (2005), pp. 5405-5432.
Joslin et al., Organometallics, 1992, 11, pp. 1749-1752.

* cited by examiner

*Primary Examiner* — Charanjit Aulakh
(74) *Attorney, Agent, or Firm* — Young & Thompson

(57) ABSTRACT

Ethereal solvents to precipitate [ruthenium (arene) (phosphorus ligand) (halogen)] complexes result in complexes having reduced stability. The stability of [ruthenium (arene) (phosphorus ligand) (halogen)] complexes is improved when the complexes are triturated or precipitated with at least one alkane. The at least one alkane can be pentane isomers, hexane isomers, heptane isomers, octane isomers and combinations thereof.

19 Claims, No Drawings

PROCESS FOR PREPARING CATIONIC RUTHENIUM COMPLEXES

CROSS-REFERENCE TO RELATED APPLICATIONS

This application is the U.S. National Phase application of PCT International Application No. PCT/GB2009/051642, filed Dec. 3, 2009, and claims priority of British Patent Application No. 0822064.2, filed Dec. 3, 2008, the disclosures of both of which are incorporated herein by reference in their entirety for all purposes.

FIELD OF THE INVENTION

The invention relates to a process for preparing ruthenium complexes and, in particular, for the large-scale manufacture of cationic [ruthenium (arene) (phosphorus ligand) (halogen)] complexes.

BACKGROUND OF THE INVENTION

EP0366390B (Takasago International Corporation) relates to ruthenium complexes containing BINAP. Faraone et al (Inorganica Chimica Acta, 34 (1979) L251-L253) relates to neutral binuclear and cationic mononuclear $\eta^6$-benzeneruthenium(II) complexes containing neutral bidentate ligands. The article describes that cationic complexes of [($\eta^6$—$C_6H_6$)Ru{$Ph_2E(CH_2)_n EPh_2$}Cl]Cl (E=P, As n=2; E=P, n=3, 4) are produced on reaction of [($\eta_6$-$C_6H_6$)RuCl$_2$]$_2$ with the bidentate ligands $Ph_2P(CH_2)_n PPh_2$ (n=2, 3, 4) and $Ph_2As(CH_2)_n AsPh_2$, in a molar ratio 1:2, in refluxed ethanol.

SUMMARY OF THE INVENTION

We have developed a process that is more suited than prior art methods to the large-scale manufacture of cationic ruthenium complexes.

Accordingly, the invention provides a process for preparing a cationic [ruthenium (arene) {4,4'-bis(disubstituted-phosphino)-3,3'-bipyridine} (halogen)] complex comprising the step of reacting [ruthenium (arene) (halogen)$_2$]$_2$ and a 4,4'-bis(disubstituted-phosphino)-3,3'-bipyridine ligand in a solvent consisting of at least one alcohol.

DETAILED DESCRIPTION OF THE INVENTION

Preferably, the arene is an unsubstituted or substituted benzene wherein the substituents are selected from straight or branched chain $C_{1-6}$ alkyl, straight or branched chain $C_{1-6}$ alkoxy, straight or branched chain $C_{1-6}$ carboalkoxy, —OH or $NO_2$. More preferably, the arene is selected from the group consisting of benzene, cymene, toluene, xylene, trimethylbenzene, hexamethylbenzene, ethylbenzene, t-butylbenzene, cumene (isopropylbenzene), anisole (methoxybenzene), methylanisole, chlorobenzene, dichlorobenzene, trichlorobenzene, bromobenzene, fluorobenzene, methylbenzoate and methyl methyl benzoate (e.g. methyl 2-methylbenzoate). Even more preferably, the arene is benzene, p-cymene or mesitylene (1,3,5-trimethylbenzene).

The halogen may be selected from the group consisting of chlorine, bromine and iodine, preferably, chlorine.

In a preferred embodiment, the [ruthenium (arene) (halogen)$_2$]$_2$ is [RuCl$_2$(p-cymene)]$_2$, [RuCl$_2$(benzene)]$_2$ or [RuCl$_2$(mesitylene)]$_2$.

Preferably, the 4,4'-bis(disubstituted-phosphino)-3,3'-bipyridine ligand is as described in GB2332201 (Hong Kong Polytechnic) wherein the 4,4'-bis(disubstituted-phosphino)-3,3'-bipyridine ligand is a chiral pyridylphosphine having the formula (I):

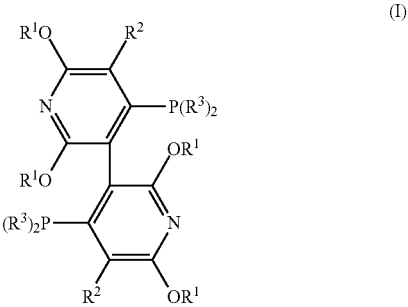

wherein:
(a) $R^1$ represents a hydrogen atom or a straight or branched-chain alkyl group having from 1 to 6 carbon atoms;
(b) $R^2$ is chosen from the following group:
  hydrogen atoms;
  halogen atoms;
  straight or branched-chain alkyl groups having 1 to 6 carbon atoms;
  straight or branched-chain alkoxy groups having from 1 to 6 carbon atoms;
  hydroxyl groups;
  straight or branched-chain chiral hydroxyalkyl groups having from 1 to 6 carbon atoms;
  amino groups; and
  mono- and di-alkylamino groups in which the alkyl group has from 1 to 6 carbon atoms;
  vinyl groups; and
  allyl groups; and
(c) $R^3$ is chosen from the following groups: straight or branched chain $C_{1-4}$ alkyl (such as methyl, ethyl, n-propyl, isopropyl, n-butyl, isobutyl or t-butyl); or

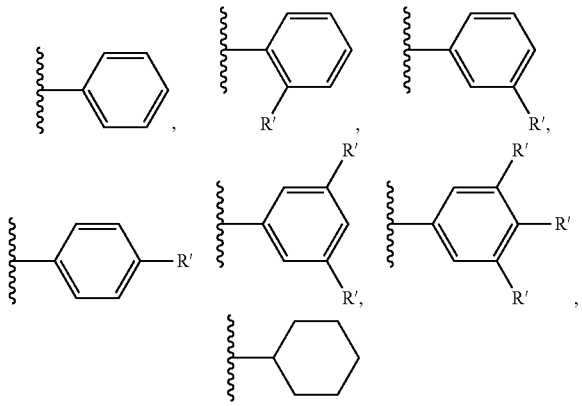

in which R' represents a straight or branched chain alkyl group having from 1 to 6 carbon atoms, a straight or branched-chain alkoxy group having from 1 to 6 carbon atoms or an amino group and, where there is more than one group R', each R' may be the same or different from the others; or
the group $P(R_3)_2$ may form a group chosen from the following:

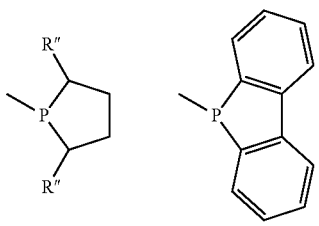

in which R" is a straight or branched-chain alkyl group having from 1 to 6 carbon atoms.

Particularly preferred examples of 4,4'-bis(disubstituted-phosphino)-3,3'-bipyridine ligands are PPhos (2,2',6,6'-tetramethoxy-4,4'-bis-(diphenylphosphino)-3,3'-bipyridine), TolPPhos (2,2',6,6'-tetramethoxy-4,4'-bis[di(p-tolyl)phosphino]-3,3'-bipyridine) and XylPPhos (2,2',6,6'-tetramethoxy-4,4'-bis[di(3,5-dimethylphenyl)phosphino]-3,3'-bipyridine).

The amount of the 4,4'-bis(disubstituted-phosphino)-3,3'-bipyridine ligand is preferably in excess of the [ruthenium (arene) (halogen)$_2$]$_2$ compound. This advantageously eliminates the need for Celite™ filtration and ensures that no [ruthenium (arene) (halogen)$_2$]$_2$ remains unreacted. Preferably the molar ratio of the 4,4'-bis(disubstituted-phosphino)-3,3'-bipyridine ligand to [ruthenium (arene) (halogen)$_2$]$_2$ compound is ≥1:1 and more preferably ≥2:1. In a particularly preferred embodiment, the molar ratio of the 4,4'-bis(disubstituted-phosphino)-3,3'-bipyridine ligand to the [ruthenium (arene) (halogen)$_2$]$_2$ compound is 2.05:1.

The [ruthenium (arene) (halogen)$_2$]$_2$ compound and the 4,4'-bis(disubstituted-phosphino)-3,3'-bipyridine ligand are combined in at least one alcohol. There are several advantages associated with using an alcoholic solvent. One advantage is that the cationic [ruthenium (arene) {4,4'-bis(disubstituted-phosphino)-3,3'-bipyridine} (halogen)] complex may be used as a catalyst in a hydrogenation reaction without the requirement of a solvent change. This is because the cationic [ruthenium (arene) {4,4'-bis(disubstituted-phosphino)-3,3'-bipyridine} (halogen)] complex can be produced in a very clean reaction (as determined by $^{31}$P-NMR), which permits the alcoholic solvent systems to be used directly in a subsequent hydrogenation reaction. Another advantage is the possibility of isolating the cationic [ruthenium (arene) {4,4'-bis(disubstituted-phosphino)-3,3'-bipyridine} (halogen)] complex with a suitable shelf life.

Suitable alcohols have boiling points at atmospheric pressure (i.e. 1.0135×10$^5$ Pa) below 120° C., more preferably below 110° C. and even more preferably below 100° C. Preferably the alcohol is dry. Preferred examples are methanol, ethanol, n-propanol, isopropanol or combinations thereof. When the cationic [ruthenium (arene) {4,4'-bis(disubstituted-phosphino)-3,3'-bipyridine} (halogen)] complex is isolated, methanol is most preferred. The molar concentration of the cationic [ruthenium (arene) {4,4'-bis(disubstituted-phosphino)-3,3'-bipyridine} (halogen)] complex in the least one alcohol is preferably between about 0.1-1 M and more preferably about 0.2-0.5 M.

In combining the [ruthenium (arene) (halogen)$_2$]$_2$ compound and a 4,4'-bis(disubstituted-phosphino)-3,3'-bipyridine ligand in the at least one alcohol, the components may be mixed in any order, although preferably the at least one alcohol is added to the [ruthenium (arene) (halogen)$_2$]$_2$ and 4,4'-bis(disubstituted-phosphino)-3,3'-bipyridine.

After the addition of the at least one alcohol, preferably the reaction mixture is stirred at a temperature in the range of −20 to 100° C., preferably −10 to 80° C. and most preferably 0 to 70° C.

The mixture may be stirred for a period e.g. preferably 1 minute to 3 hours, more preferably 2 minutes to 2 hours and most preferably 2.5 minutes to 1.5 hours. The reaction preferably occurs under an inert atmosphere, such as nitrogen or argon. A cationic ruthenium compound in an alcohol is formed, which is preferably a clear solution.

The solution of cationic [ruthenium (arene) {4,4'-bis(disubstituted-phosphino)-3,3'-bipyridine} (halogen)] complex in the at least one alcohol may be used directly, if the application requires an alcoholic solvent.

However, it may be desirable to recover the cationic ruthenium complex, for example, by removing the at least one alcohol.

In another aspect, the present invention provides a process for preparing a solid cationic [ruthenium (arene) (phosphorus ligand) (halogen)] complex comprising the step of treating the complex with at least one alkane.

The inventors have found that the use of ethereal solvents, such as methyl tert-butyl ether (MTBE), to precipitate [ruthenium (arene) (phosphorus ligand) (halogen)] complexes result in complexes having reduced stability. For example, isolated dry samples of [(S)-XylPPhos RuCl (p-cymene)]Cl and [(S)-XylPPhos RuCl (benzene)]Cl which are precipitated with MTBE are found to retain MTBE that cannot be removed by drying and to degrade significantly even when stored under nitrogen or in a glove box over short periods of time (2-4 weeks) giving major impurities by $^{31}$P-NMR. This is a disadvantage as the shelf life of the catalysts is greatly reduced and batch variations become significant.

Surprisingly, the inventors have now found that the stability of [ruthenium (arene) (phosphorus ligand) (halogen)] complexes, including the cationic [ruthenium (arene) {4,4'-bis(disubstituted-phosphino)-3,3'-bipyridine} (halogen)] complexes discussed above, is improved when the complexes are triturated or precipitated with at least one alkane. Without wishing to be bound by theory, it is believed that the complex stability is linked to the size and type of the solid or crystal formed and that the at least one alkane improves the quality of the solid or crystals. The inventors have further found that the solid complex prepared is easily handled and may be easily removed from the reaction vessel.

The arene and halogen are preferably selected from those discussed above in connection with the cationic [ruthenium (arene) {4,4'-bis(disubstituted-phosphino)-3,3'-bipyridine} (halogen)] complexes.

Any suitable phosphorus compound capable of forming a ligand-metal interaction with the Ru atom may be used. In the ligand, each phosphorus atom is covalently bonded to three carbon atoms (tertiary phosphines).

The phosphorus ligand may be monodentate, e.g. PPh$_3$, or bidentate. The ligand may be chiral or achiral, although in many instances it is preferred that the phosphorus ligand is chiral. A variety of chiral phosphorus ligands has been described and reviews are available, for example see W. Tang and X. Zhang, Chem. Rev. 2003, 103, 3029-3070, H. Shimizu et al, Tetrahedron, 2005, 61, 5405-5432 and J. C. Carretero, Angew. Chem. Int. Ed., 2006, 45, 7674-7715, each of which is incorporated herein by reference in its entirety for all purposes. Phosphorus ligands that may be used in the present invention include but are not restricted to the following structural types:

BINAP, R = aryl and alkyl

P—PHOS
R = aryl, alkyl

H⁸—BINAP, R = aryl and alkyl

BITIANAP
R = aryl, alkyl
X = O, S, N

TMBITIOP
R = aryl, alkyl
X = O, S, N

R = aryl, alkyl
X = O BIBFUP
X = NH or S

Substituted Biphenyl:
R = aryl and alkyl
R¹ = alkyl, alkoxy
R² = H, alkyl, alkoxy, halide
R³ = H, alkyl including:

$C_n$ TUNAPHOS

R¹ = OMe: BIPHEP
R¹ = OMe, R² = Cl: Cl, MeO BIPHEP
R¹ and R³ = Me, R² = OMe: BIMOP
R¹ = Me: BIPHEMP
R¹ and R³ = Me: TETRAPHEMP
R¹, R², and R³ = Me: HEXAPHEMP

SEGPHOS

SYNPHOS

PARAPHOS
X = functional group
R = aryl, alkyl including X = H:

PHANEPHOS

BIPNOR

CHIRAPHOS
R¹ = R² alkyl
PROPHOS
R² = alkyl R¹ = H

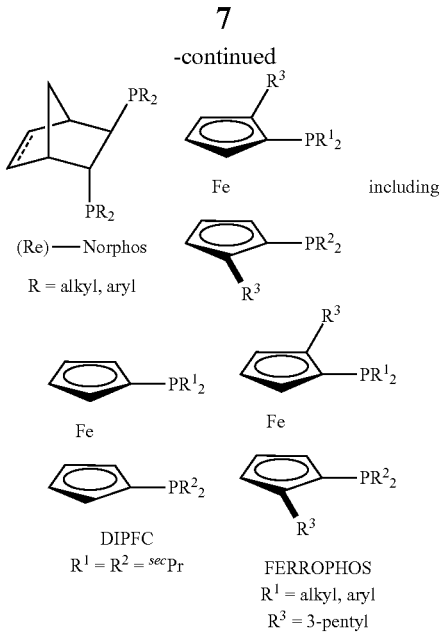

In the above structures —PR$_2$ may be —P(alkyl)$_2$ in which alkyl is preferably C$_1$-C$_{10}$ alkyl, —P(aryl)$_2$ where aryl includes phenyl and naphthyl which may be substituted or unsubstituted. —PR$_2$ is preferably either —P(aryl)$_2$ where aryl includes phenyl, tolyl or xylyl. Alternatively, the R groups on the P-atom may be linked as part of a cyclic structure.

Substituting groups may be present on the alkyl or aryl substituents in the phosphorus ligands. Such substituting groups are typically branched or linear C$_{1-6}$ alkyl groups such as methyl, ethyl, propyl, isopropyl, tert butyl, or C$_{3-6}$ cycloalkyl groups such cyclohexyl.

The phosphorus ligands are preferably used in their single enantiomer form. These phosphorus ligands are generally available commercially and their preparation is known. For example, the preparation of 4,4'-bis(disubstituted-phosphino)-3,3'-bipyridine ligands is given in GB2332201.

Preferred examples of the phosphorus ligand are PPhos, TolPPhos, XylPPhos, BINAP, TolBINAP or XylBINAP.

When the cationic [ruthenium (arene) (phosphorus ligand) (halogen)] complex is a cationic [ruthenium (arene) {4,4'-bis(disubstituted-phosphino)-3,3'-bipyridine} (halogen)] complex, the complex may be prepared by the method described above i.e. by reacting [ruthenium (arene) (halogen)$_2$]$_2$ and a 4,4'-bis(disubstituted-phosphino)-3,3'-bipyridine ligand in a solvent consisting of at least one alcohol.

When the cationic [ruthenium (arene) (phosphorus ligand) (halogen)] complex is treated with the at least one alkane, the complex may be in the form of a solid. If desired, however, the cationic complex may be in the form of a slurry or a solution.

Within the context of the present invention, "solution" means a homogeneous mixture of the cationic complex in one or more solvents. The solution may be prepared in a number of ways, for example, the solid cationic complex may be dissolved in a suitable solvent or solvent mixture. This may be appropriate when the cationic complex has been previously isolated as a solid and there is a need to increase its storage stability. Alternatively, the solvent or solvent mixture used to prepare the cationic complex itself may be either treated directly with the at least one alkane or processed into a slurry as described below before treatment with the at least one alkane. In this instance, it can be seen that the intermediate isolation of solid cationic complex is not required.

"Slurry" means a heterogeneous mixture of at least a portion of the solid cationic complex in one or more solvents. "Slurry" therefore includes a mixture of cationic complex which is partially present as a solid, as well as being partially dissolved in the one or more solvents. The slurry may be prepared by suspending the solid complex in a solvent or solvent mixture. Alternatively, the slurry may be prepared by concentrating a solution of the complex, such as by increasing the temperature or reducing the pressure using distillation or stripping methods well known in the art. In a preferred embodiment, the solution is heated under vacuum to strip off the solvent or solvent mixture until a slurry of the cationic complex is obtained. Stripping solvent mixtures will result in a change in the relative amounts of each solvent in the solvent mixture.

When the solvent mixture has been concentrated, it may be desirable to further readjust the relative amounts of each solvent in the solvent mixture by the addition of solvent. For example, when the solvent mixture is toluene and methanol, the mixture may be concentrated to remove different amounts of toluene and methanol. In this instance, a suitable volume of methanol may then be subsequently added to the concentrated mixture to increase the relative amount of methanol.

The slurry or solution of the cationic [ruthenium (arene) (phosphorus ligand) (halogen)] preferably comprises at least one alcohol, aromatic hydrocarbon or combinations thereof. In one embodiment, the slurry or solution consists of one or more alcohols. In another embodiment, the slurry or solution consists of one or more alcohols and one or more aromatic hydrocarbons. The alcohols that can be used are as defined above in connection with the cationic [ruthenium (arene) {4,4'-bis(disubstituted-phosphino)-3,3'-bipyridine} (halogen)] complexes. Preferably the alcohol is dry. Preferred examples are methanol, ethanol, isopropanol, n-propanol or combinations thereof. By "aromatic hydrocarbons" we mean liquid arenes having boiling points at atmospheric pressure (i.e. $1.0135 \times 10^5$ Pa) below 220° C., more preferably below 200° C. and even more preferably below 180° C. Preferred examples are benzene, toluene, dimethylbenzene (such as o-, m- or p-xylene), trimethylbenzene (such as 1,2,3-, 1,2,4- or 1,3,5-trimethylbenzene) or combinations thereof. When the cationic [ruthenium (arene) (phosphorus ligand) (halogen)] complex is a [ruthenium (arene) {4,4'-bis(disubstituted-phosphino)-3,3'-bipyridine} (halogen)] complex, the aromatic hydrocarbon used is conveniently the same as that present as the coordinated arene ligand in the [Ru (arene) (halogen)$_2$]$_2$ complex. In one preferred embodiment, the slurry or solution comprises methanol and toluene.

In a preferred embodiment, the present invention provides a process for preparing a solid cationic [ruthenium (arene) (phosphorus ligand) (halogen)] complex comprising the step of treating a solution or slurry of the complex with at least one alkane wherein the arene is benzene, p-cymene or mesitylene, the phosphorus ligand is PPhos, TolPPhos, XylPPhos, BINAP, TolBINAP or XylBINAP.

The alkane utilised is preferably a straight or branched C$_{1-10}$ alkane. Preferred examples are pentane isomers, hexane isomers, heptane isomers, octane isomers or combinations thereof. Particularly preferred examples are n-hexane, isohexane, n-heptane or combinations thereof. An especially preferred alkane is n-hexane.

Any suitable quantity of the alkane may be used.

When the slurry or solution of the cationic complex is treated with the at least one alkane, the stabilised cationic complex may precipitate or crystallise immediately. In one embodiment of the invention, however, a two-phase solvent mixture is obtained when the slurry or solution of the cationic complex is treated with the at least one alkane. In this instance, strong agitation of the two-phase system may be suitable during subsequent processing in order to prepare the stabilised cationic complex.

The cationic ruthenium complex may be recovered in a process further comprising:
  (a) evaporating the slurry or solution comprising the at least one alkane;
  (b) triturating the solid of step (a) with at least one alkane, wherein the at least one alkane may be the same or different to the at least one alkane of step (a); and
  (c) recovering the solid cationic [ruthenium (arene) (phosphorus ligand) (halogen)] complex.

Here, the solution comprising the at least one alkane is removed in order to increase the concentration of cationic ruthenium complex. This may be achieved by increasing the temperature or reducing the pressure using distillation or stripping methods well known in the art. In a preferred embodiment, the solution is heated under vacuum to strip off solvents until crystallisation of the cationic ruthenium complex occurs and is continued until all the solvents have been removed. Thus the product after evaporation of the solution comprising the at least one alkane is preferably a solid of the cationic ruthenium complex.

The solid obtained after evaporating the solution comprising the at least one alkane is then triturated. The at least one alkane utilised to triturate the solid may be the same or different to the at least one alkane of step (a). Preferably, the at least one alkane of steps (a) and (b) are the same. Most preferably, the at least one alkane of steps (a) and (b) is hexane.

The solid cationic [ruthenium (arene) (phosphorus ligand) (halogen)] complex may be recovered directly by filtering, decanting or centrifuging. If desired a proportion of the alkane and any residual solvent mixture may be evaporated prior to the recovery of the complex.

Alternatively, the solid cationic [ruthenium (arene) (phosphorus ligand) (halogen)] complex may be recovered simply by evaporating the at least one alkane or evaporating the slurry or solution comprising the at least one alkane.

Howsoever the complex is recovered, the separated complex is preferably dried. Drying may be performed using known methods, for example, at temperatures in the range of 10-60° C. and preferably 20-40° C. under 0.1-30 mbar for 1 hour to 5 days.

The complexes prepared by the processes of the present invention are pure and may be used in catalytic applications as obtained or further dried. Furthermore, the catalysts obtained using the present method are storage stable, as well as being free flowing solids which are easy to handle. By "storage stable" we mean that <15%, and more preferably <10%, of impurities are formed on storing the catalysts at 20° C. under inert conditions for at least two weeks. The methods therefore are suited to large-scale manufacture and large-scale catalytic applications.

The invention is further illustrated by reference to the following non-limiting Examples.

EXAMPLES

General Remarks

Anhydrous solvents were purchased from Fluka and used as received in SureSeal bottles over molecular sieves. All reagents were purchased from commercial sources and used without further purification.

[(S)-XylPPhos RuCl (p-cymene)]Cl (Comparative Example)

To a mixture of [RuCl$_2$ (p-cymene)]$_2$ (1.531 g, 2.5 mmol) and (S)-XylPPhos (3.878 g, 5.1 mmol) under nitrogen was added dry toluene (2 mL) and dry EtOH (6 mL) and solution heated to 55° C. for 1 hour. At this stage $^{31}$P NMR confirmed the reaction was complete and the solvent was evaporated. The resulting solid was triturated with MTBE. The product was then isolated by filtration and drying to give the title compound as an orange solid (>95% yield, >98% pure by $^1$H and $^{31}$P NMR in C$_6$H$_6$). This compound [(S)-XylPPhos RuCl (p-cymene)]Cl*⅓ MTBE, when stored in the glove box over two weeks, showed a significant degradation as determined by $^{31}$P NMR (>30%).

Using dichloromethane instead of toluene gave an initial purity of >98% by $^1$H and $^{31}$P NMR in C$_6$H$_6$ and showed a similar degradation when stored in the glove box.

Example 1

Synthesis of [(XylPPhos RuCl(p-cymene)]Cl

Initial investigations were undertaken using the procedure for [(S)-XylPPhos RuCl (p-cymene)]Cl 2 mmol scale and principally using neat alcoholic solvents with reaction mixtures at concentrations of 0.25 M.

The synthesis of [(S)-XylPPhos RuCl (p-cymene)]Cl was achieved by stirring the dimer [RuCl$_2$(p-cymene)]$_2$ (1eg.) and (S)-XylPPhos (2.05 eq.) in dry MeOH (0.25M) at 55° C. under nitrogen for 1 hour. At this stage $^{31}$P NMR confirmed the reaction was complete and as the phosphine was in excess, no filtration over celite was necessary.

This procedure was successfully repeated with EtOH and i-PrOH and $^{31}$P NMR of reaction solutions showed very clean formation of the required catalyst providing evidence that neat alcoholic solvent systems would be applicable for direct use in reaction.

Trituration with MTBE

The solvent was evaporated and the resulting solid triturated with MTBE. The product was then isolated by filtration and drying to give [(S)-XylPPhos RuCl (p-cymene)]Cl*⅓ MTBE as an orange solid (>95% yield, >98% pure by $^1$H and $^{31}$P NMR).

This compound when stored in the glove box over two weeks still showed, however, a significant degradation determined by $^{31}$P NMR (>30%).

Example 2

(S)-XylPPhos RuCl (p-cymene)]Cl

To a mixture of [RuCl$_2$ (p-cymene)]$_2$ (3.06 g, 5 mmol) and (S)-XylPPhos (7.75 g, 10.25 mmol) under nitrogen was added dry MeOH (40 mL) and solution heated to 55° C. for 1 hour. At this stage $^{31}$P NMR confirmed the reaction was complete, solution diluted with hexane (250 mL), solvent was evaporated and the resulting solid triturated with hexane (250 mL). The product was then isolated by filtration and drying to give the title compound as a brown solid (>95% yield, >98% pure by $^1$H and $^{31}$P NMR).

[(S)-XylPPhos RuCl (p-cymene)]Cl

To a mixture of [RuCl$_2$ (p-cymene)]$_2$ (612 mg, 1 mmol) and (S)-XylPPhos (1.55 g, 2.05 mmol) under nitrogen was added dry EtOH (8 mL) and solution heated to 55° C. for 1 hour. At this stage $^{31}$P NMR confirmed the reaction was complete, solution diluted with hexane (50 mL) solvent was evaporated and the resulting solid triturated with hexane (50 mL). The product was then isolated by filtration and drying to give the title compound as a brown solid (>95% yield, >98% pure by $^1$H and $^{31}$P NMR).

[(S)-XylPPhos RuCl (p-cymene)]Cl

To a mixture of [RuCl$_2$ (p-cymene)]$_2$ (612 mg, 1 mmol) and (S)-XylPPhos (1.55 g, 2.05 mmol) under nitrogen was added dry $^i$PrOH (20 mL) and solution heated to 55° C. for 1 hour. At this stage 31P NMR confirmed the reaction was complete, solution diluted with hexane (50 mL) solvent was evaporated and the resulting solid triturated with hexane (50 mL). The product was then isolated by filtration and drying to give the title compound as a brown solid (>95% yield, >98% pure by $^1$H and $^{31}$P NMR).

[(S)-PPhos RuCl (p-cymene)]Cl

To a mixture of [RuCl$_2$ (p-cymene)]$_2$ (612 mg, 1 mmol) and (S)-PPhos (1.32 g, 2.05 mmol) under nitrogen was added dry MeOH (8 mL) and solution heated to 55° C. for 1 hour. At this stage $^{31}$P NMR confirmed the reaction was complete, solution diluted with hexane (50 mL) solvent was evaporated and the resulting solid triturated with hexane (50 mL). The product was then isolated by filtration and drying to give the title compound as a brown solid (>95% yield, >98% pure by $^1$H and $^{31}$P NMR).

Example 3

[(S)-XylPPhos RuCl (benzene)]Cl

To a mixture of [RuCl$_2$ (benzene)]$_2$ (500 mg, 1 mmol) and (S)-XylPPhos (1.55 g, 2.05 mmol) under nitrogen was added dry toluene (4 mL) and dry MeOH (12 mL) and solution heated to 55° C. for 1 hour. At this stage $^{31}$P NMR confirmed the reaction was complete, solution diluted with hexane (50 mL), solvent was evaporated and the resulting solid triturated with hexane (50 mL). The product was then isolated by filtration and drying to give the title compound as a brown solid (>95% yield, >98% pure by $^1$H and $^{31}$P NMR).

[(R)-XylPPhos RuCl (benzene)]Cl

To a mixture of solids made up from 5 g of [RuCl$_2$ (benzene)]$_2$ and 15.52 g of (R)-XylPPhos (2.05 eq) was added 10 ml of toluene and 100 ml of methanol. The resulting slurry was stirred for 1.3 hours at 55° C. The resulting brown-red solution was stripped at a bath temperature of 40° C. keeping an internal pressure of 180-250 mbar until approx 70 ml of solvent mixture was stripped. To the remaining solution in 40 ml of solvent was added 160 ml of n-hexane resulting in a brown-red lower phase and a clear upper phase. Stripping the mixture with strong agitation at a bath temperature of 40° C. keeping an internal pressure of 30-300 mbar resulted in a brown crystalline solid, that was triturated with 50 ml of n-hexane and transferred onto a sinter funnel using 2×30 ml of further n-hexane. After a filtration the compound was dried for 3 days at <1 mbar. 19.8 g of the title compound was obtained as a coarse solid with a high purity by $^1$H and $^{31}$P NMR (>98%) in CD$_3$OD and CDCl$_3$.

[(S)-PPhos RuCl (benzene)]Cl

To a mixture of [RuCl$_2$ (benzene)]$_2$ (500 mg, 1 mmol) and (S)-PPhos (1.32 g, 2.05 mmol) under nitrogen was added dry toluene (4 mL) and dry MeOH (12 mL) and solution heated to 55° C. for 1 hour. At this stage $^{31}$P NMR confirmed the reaction was complete, solution diluted with hexane (50 mL), solvent was evaporated and the resulting solid triturated with hexane (50 mL). The product was then isolated by filtration and drying to give the title compound as a brown solid (>95% yield, >98% pure by $^1$H and $^{31}$P NMR).

[(R)-PPhos RuCl (benzene)]Cl

To a mixture of solids made up from 5 g of [RuCl$_2$ (benzene)]$_2$ and 13.21 g of (R)-PPhos (2.05 eq) was added 20 ml of toluene and 100 ml of methanol. The resulting slurry was stirred for 1.3 hours at 55° C. The resulting brown-red solution was stripped at a bath temperature of 40° C. keeping an internal pressure of 180-250 mbar until approx 90 ml of solvent mixture was stripped. To the remaining slurry in 30 ml of solvent was added 10 ml of methanol and 160 ml of n-hexane resulting in a brown-red lower phase and a clear upper phase. The mixture was stripped and worked up as in the same scale synthesis of [(R)-XylPPhos RuCl (benzene)] Cl. After drying 17.8 g of the title compound was obtained as a coarse solid with a high purity by $^1$H and $^{31}$P NMR (>98%) in CD$_3$OD and CDCl$_3$.

[(S)-BINAP RuCl (benzene)]Cl

To a mixture of [RuCl$_2$ (benzene)]$_2$ (500 mg, 1 mmol) and (S)-BINAP (1.25 g, 2.05 mmol) under nitrogen was added dry toluene (4 mL) and dry MeOH (12 mL) and solution heated to 55° C. for 1 hour. At this stage $^{31}$P NMR confirmed the reaction was complete, solution diluted with hexane (50 mL), solvent was evaporated and the resulting solid triturated with hexane (50 mL). The product was then isolated by filtration and drying to give the title compound as a brown solid (>95% yield, >98% pure by $^1$H and $^{31}$P NMR).

[(S)-BINAP RuCl (benzene)]Cl

To a mixture of solids made up from 5 g of [RuCl$_2$ (benzene)]$_2$ and 12.77 g of (S)-Binap (2.05 eq) was added 20 ml of toluene and 100 ml of methanol. The procedure as for [(R)-PPhos RuCl (benzene)]Cl was repeated and 17.5 g of the title compound was obtained as a coarse solid with a high purity by $^1$H and $^{31}$P NMR (>98%) in CD$_3$OD and CDCl$_3$.

[(S)-BINAP RuCl (p-cymene)]Cl

To a mixture of [RuCl$_2$ (p-cymene)]$_2$ (9.61 g, 15.7 mmol) and (S)-BINAP (20 g, 32.2 mmol) under nitrogen was added dry MeOH (128 mL) and solution heated to 55° C. for 1 hour. At this stage $^{31}$P NMR confirmed the reaction was complete and the solution was diluted with n-hexane (500 mL) forming a two-phase mixture. The solvent was evaporated and the resulting solid was triturated with n-hexane (500 mL). The product was then isolated by filtration and drying to give the title compound as a coarse orange solid (>95% yield, >98% pure by $^1$H and $^{31}$P NMR in C$_6$D$_6$).

The synthesis was repeated using (R)-BINAP (20 g, 32.2 mmol) with similar results. Both batches when analysed by $^1$H and $^{31}$P NMR in C$_6$D$_6$ and CDCl$_3$ showed no decomposition upon storage.

[(R)-TolBINAP RuCl (p-cymene)]Cl

To a mixture of [RuCl$_2$ (p-cymene)]$_2$ (306 mg, 0.5 mmol) and (R)-TolBinap (696 mg, 1.025 mmol) under nitrogen was added dry MeOH (4 mL) and solution heated to 55° C. for 1 hour. At this stage $^{31}$P NMR confirmed the reaction was complete and the solution was diluted with n-hexane (25 mL). Then the solvent mixture was stripped. The resulting solid was triturated with n-hexane (25 mL). The product was then isolated by filtration and drying to give the title compound as an orange solid (>95% yield, >98% pure by $^1$H and $^{31}$P NMR in C$_6$D$_6$). No decomposition was observed after 6 weeks of storage in the glove box under nitrogen.

[(S)-XylBINAP RuCl (benzene)]Cl To a mixture of solids made up from 0.5 g of [RuCl$_2$ (benzene)]$_2$ and 1.51 g of (S)-XylBinap (2.05 eq) was added 1 ml of toluene and 10 ml of methanol. The resulting slurry was stirred for 0.5 hours at 55° C. The resulting brown-red solution was stripped at a bath temperature of 40° C. keeping an internal pressure of 180-250 mbar until approx 7 ml of solvent mixture was stripped. To the remaining solution in 4 ml of solvent was added 20 ml of n-hexane resulting in a brown-red lower phase and a clear upper phase. Stripping the mixture with strong agitation at a bath temperature of 40° C. keeping an internal pressure of 30-300 mbar resulted in a brown crystalline solid, that was triturated with 10 ml of n-hexane and transferred onto a sinter funnel using 2×10 ml of further n-hexane. After a filtration the compound was dried for 3 days at <1 mbar. 1.86 g of the title compound was obtained as a coarse solid with a high purity by $^1$H and $^{31}$P NMR (>98%) in $CD_3OD$ and $CDCl_3$.

Example 3

Stability Studies

The table below details the short term stability of catalysts prepared by the methods provided above. Following initial analysis by $^{31}$P NMR, the isolated solids were stored under nitrogen in a glove box for two weeks and once again analysed by $^{31}$P NMR. The solids were then removed from the glove box and stored in air on the bench for a further two weeks before finally analysing again by $^{31}$P NMR.

TABLE 1

Catalyst stability

| Catalyst | NMR Solvent | Trituration Solvent | Start Imp % (NMR) | Glove Box Imp % (NMR) | Bench Imp % (NMR) |
|---|---|---|---|---|---|
| (S)-XylPPhos RuCl(p-cymene)]Cl | $C_6D_6$ | MTBE | 3 | 40 | dec |
| (S)-XylPPhos RuCl(p-cymene)]Cl | $C_6D_6$ | Hexane | 0 | 0 | 10 |
| (S)-PPhos RuCl(p-cymene)]Cl | $C_6D_6$ | Hexane | 1 | 3 | 6 |
| (S)-BINAP RuCl(p-cymene)]Cl | $C_6D_6$ | Hexane | 0 | 0 | 5 |
| (S)-XylPPhos RuCl(benzene)]Cl | $CD_3OD$ | Hexane | 3 | 6 | 14 |
| (S)-PPhos RuCl(benzene)]Cl | $CD_3OD$ | Hexane | 1 | 4 | 9 |
| (S)-BINAP RuCl(benzene)]Cl | $CD_3OD$ | Hexane | 0 | 0 | 10 |

NMR conditions: 30 mg of catalyst was dissolved in 1 mL of deuterated solvent and samples analysed by $^{31}$P (1024 scans) and $^1$H (32 scans) NMR; dec = decomposition.

The sample prepared by MTBE trituration was shown to degrade significantly while stored in the glovebox over two weeks showing 40% impurities by $^{31}$P NMR.

All the samples prepared by hexane trituration, however, showed good stability in the glovebox over two weeks. The samples when stored on the bench in air also showing considerably less degradation than the sample prepared by MTBE trituration.

A sample of (S)-XylPPhos RuCl (p-cymene) Cl was stored for 18 months in the glove box and then analysed. The sample was found to contain <3% impurities as assayed by $^{31}$P NMR in $C_6H_6$.

These results clearly show that catalysts prepared by trituration from hexane showed a significant advantage in terms of storage stability over the catalysts prepared by trituration from MTBE.

The invention claimed is:

1. A process for preparing a solid cationic [ruthenium (arene) (phosphorus ligand) (halogen)] complex, comprising:
   treating the complex with at least one alkane selected from the group consisting of hexane isomers, heptane isomers, octane isomers and combinations thereof.

2. The process according to claim 1, wherein the arene is an unsubstituted or substituted benzene, wherein the substituents are selected from the group consisting of straight or branched chain C1-6 alkyl, straight or branched chain C1-6 alkoxy, straight or branched chain C1-6 carboalkoxy, —OH and NO2.

3. The process according to claim 2, wherein the arene is selected from the group consisting of benzene, cymene, toluene, xylene, trimethylbenzene, hexamethylbenzene, ethylbenzene, t-butylbenzene, cumene, anisole, methylanisole, chlorobenzene, dichlorobenzene, trichlorobenzene, bromobenzene, fluorobenzene, methyl benzoate and methyl methylbenzoate.

4. The process according to claim 3, wherein the arene is selected from the group consisting of benzene, p-cymene and 1,3,5-trimethylbenzene.

5. The process according to claim 1, wherein the phosphorus ligand is chiral or achiral, monodentate or bidentate phosphorus ligand in which each phosphorus atom is covalently bonded to 3 carbon atoms.

6. The process according to claim 5, wherein the phosphorus ligand is selected from the group consisting of PPhos, TolPPhos, XylPPhos, BINAP, TolBINAP and XylBINAP.

7. The process according to claim 1, wherein the alkane is selected from the group consisting of n-hexane, isohexane, n-heptane and combinations thereof.

8. The process according to claim 1, wherein the complex is in the form of a solid when treated with the at least one alkane.

9. The process according to claim 1, wherein the complex is in the form of a slurry or a solution when treated with the at least one alkane.

10. The process according to claim 9, wherein the slurry or solution comprises at least one alcohol, aromatic hydrocarbon or combinations thereof.

11. The process according to claim 10, wherein the alcohol has a boiling point below 120° C. at atmospheric pressure.

12. The process according to claim 11, wherein the alcohol is selected from the group consisting of methanol, ethanol, isopropanol, n-propanol and combinations thereof.

13. The process according to claim 10, wherein the aromatic hydrocarbon has a boiling point below 220° C. at atmospheric pressure.

14. The process according to claim 13, wherein the aromatic hydrocarbon is selected from the group consisting of benzene, toluene, dimethylbenzene, trimethylbenzene and combinations thereof.

15. The process according to claim 9, further comprising:
   (a) evaporating the slurry or solution comprising the at least one alkane;
   (b) triturating the solid of step (a) with at least one alkane, wherein the at least one alkane may be the same or different to the alkane of step (a); and
   (c) recovering the solid cationic complex.

16. The process according to claim 8, further comprising recovering the solid cationic [ruthenium (arene) (phosphorus ligand) (halogen)] complex.

17. The process according to claim 9, further comprising recovering the solid cationic [ruthenium (arene) (phosphorus ligand) (halogen)] complex.

18. A process for preparing a solid complex, comprising:
triturating or precipitating a complex of cationic [ruthenium (arene) (phosphorus ligand) (halogen)] with at least one alkane selected from the group consisting of hexane isomers, heptane isomers, octane isomers and combinations thereof, thereby obtaining a stabilized solid complex.

19. The process according to claim 18, wherein the complex is precipitated from an ethereal solvent.

* * * * *